(12) United States Patent
Lachenbruch (10) Patent No.: US 9,030,331 B2
(45) Date of Patent: *May 12, 2015

(54) FLUID SUPPLY CONTROL FOR PATIENT SUPPORT SURFACE

(71) Applicant: Hill-Rom Services, Inc., Batesville, IN (US)

(72) Inventor: Charles A. Lachenbruch, Lakeway, TX (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/019,002

(22) Filed: Sep. 5, 2013

(65) Prior Publication Data

US 2014/0007346 A1    Jan. 9, 2014

Related U.S. Application Data

(63) Continuation of application No. 12/881,249, filed on Sep. 14, 2010, now Pat. No. 8,531,307.

(60) Provisional application No. 61/243,622, filed on Sep. 18, 2009.

(51) Int. Cl.
*G08B 21/00* (2006.01)
*A61G 7/057* (2006.01)
(Continued)

(52) U.S. Cl.
CPC .. *A61G 7/05769* (2013.01); *A61G 2007/05792* (2013.01); *A61G 7/05* (2013.01); *A61G 7/0525* (2013.01); *A61B 5/002* (2013.01); *A61B 5/01* (2013.01); *A61B 5/1036* (2013.01);
(Continued)

(58) Field of Classification Search
CPC ...................... A61G 2007/06769; G08B 21/99
USPC ........... 340/573.1, 573.7, 575, 626, 665, 666, 340/667, 686.1; 324/204, 442, 639; 5/421, 5/423, 706, 710, 713, 727, 737, 740; 73/172
See application file for complete search history.

(56) References Cited

U.S. PATENT DOCUMENTS 5,970,789 A * 10/1999 Meyer et al. .................... 73/172
6,165,142 A    12/2000 Bar
(Continued)

FOREIGN PATENT DOCUMENTS

JP    6-502317    3/1994
JP    11-503953    4/1999
(Continued)

OTHER PUBLICATIONS

European Search Report for Application No. 10176760.6, dated Apr. 9, 2012, 6 pages.
(Continued)

*Primary Examiner* — Van Trieu
(74) *Attorney, Agent, or Firm* — Barnes & Thornburg LLP (57) ABSTRACT

A control system of a patient support surface calculates a surface performance index as a function of pressure and shear. The control system also receives information from an electronic medical record (EMR) corresponding to a person's susceptibility of developing at least one of a pressure ulcer and a superficial lesion and adjusts at least one of a component and a characteristic of the person support surface based on the information.

20 Claims, 7 Drawing Sheets

(51) Int. Cl.
*A61G 7/05* (2006.01)
*A61B 5/00* (2006.01)
*A61B 5/01* (2006.01)
*A61B 5/103* (2006.01)

(52) U.S. Cl.
CPC .............. *A61B 5/447* (2013.01); *A61B 5/6891* (2013.01); *A61B 5/6892* (2013.01); *A61B 2560/0242* (2013.01); *A61B 2562/0247* (2013.01); *A61B 2562/029* (2013.01); *A61G 7/05776* (2013.01); *A61G 2007/05784* (2013.01); *A61G 2203/32* (2013.01); *A61G 2203/34* (2013.01); *A61G 2203/46* (2013.01)

(56) References Cited

U.S. PATENT DOCUMENTS

| | | | |
|---|---|---|---|
| 6,516,483 B1* | 2/2003 | VanSteenburg | 5/737 |
| 6,560,804 B2* | 5/2003 | Wise et al. | 5/713 |
| 6,721,980 B1 | 4/2004 | Price et al. | |
| 7,030,764 B2* | 4/2006 | Smith et al. | 340/573.1 |
| 7,090,648 B2 | 8/2006 | Sackner et al. | |
| 7,107,642 B2 | 9/2006 | Wong et al. | |
| 7,111,346 B2 | 9/2006 | Inman et al. | |
| 7,219,380 B2* | 5/2007 | Beck et al. | 5/713 |
| 7,228,576 B2 | 6/2007 | Inman et al. | |
| 7,330,127 B2* | 2/2008 | Price et al. | 340/666 |
| 7,378,975 B1* | 5/2008 | Smith et al. | 340/573.1 |
| 7,409,735 B2 | 8/2008 | Kramer et al. | |
| 7,459,645 B2 | 12/2008 | Skinner et al. | |
| 7,515,059 B2 | 4/2009 | Price et al. | |
| 7,714,238 B2 | 5/2010 | Skinner et al. | |
| 7,825,814 B2 | 11/2010 | Lokhorst et al. | |
| 8,087,113 B2* | 1/2012 | Roff et al. | 5/713 |
| 8,220,090 B2* | 7/2012 | Gowda | 5/713 |
| 8,525,680 B2* | 9/2013 | Riley et al. | 340/573.1 |
| 8,531,307 B2 | 9/2013 | Lachenbruch | |
| 2005/0076715 A1 | 4/2005 | Kuklis et al. | |
| 2005/0288749 A1 | 12/2005 | Lachenbruch | |
| 2007/0135878 A1 | 6/2007 | Lachenbruch et al. | |
| 2008/0015665 A1 | 1/2008 | Lachenbruch | |
| 2008/0028533 A1 | 2/2008 | Stacy et al. | |
| 2009/0217460 A1 | 9/2009 | Bobey et al. | |
| 2010/0043143 A1* | 2/2010 | O'Reagan et al. | 5/421 |
| 2010/0132116 A1 | 6/2010 | Stacy et al. | |
| 2010/0274331 A1 | 10/2010 | Williamson et al. | |
| 2011/0068939 A1 | 3/2011 | Lachenbruch | |
| 2011/0163885 A1* | 7/2011 | Poulos et al. | 340/626 |
| 2012/0174322 A1* | 7/2012 | Skinner et al. | 5/713 |

FOREIGN PATENT DOCUMENTS

| | | |
|---|---|---|
| JP | 2000-274 A | 1/2000 |
| JP | 2003-531680 A | 10/2003 |
| JP | 2005-342443 | 12/2005 |
| JP | 2006-503649 A | 2/2006 |
| JP | 2006-515995 A | 6/2006 |
| JP | 2006-516925 A | 7/2006 |
| JP | 2008-55152 A | 3/2008 |
| JP | 2008-528123 A | 7/2008 |
| JP | 2009-517103 A | 4/2009 |
| WO | WO 00/24353 A1 | 5/2000 |
| WO | WO 2007/008831 A2 | 1/2007 |

OTHER PUBLICATIONS

Office Action dated Jul. 8, 2014, in related Japanese Patent Application No. 2010-209465, 13 pages (with English language translation).

* cited by examiner

FLUID SUPPLY CONTROL FOR PATIENT SUPPORT SURFACE

CROSS-REFERENCE TO RELATED APPLICATIONS

This application is a continuation of U.S. application Ser. No. 12/881,249, filed Sep. 14, 2010, now U.S. Pat. No. 8,531,307, which claims the benefit, under 35 U.S.C. §119(e), of U.S. Provisional Application No. 61/243,622, which was filed Sep. 18, 2009, and each of which is hereby incorporated by reference herein.

BACKGROUND

The present disclosure relates to person support surfaces such as mattresses. More particularly, the present disclosure relates to inflatable person support surfaces having controllers that regulate supply of a fluid as a function of various characteristics of the person support surfaces.

Persons lying on support surfaces, such as hospital bed mattresses, for extended periods of time are susceptible to the development of pressure ulcers (also known as decubitus ulcers or bedsores). Pressure ulcers oftentimes are lesions found adjacent to bony or cartilaginous areas. While many devices and methods have been developed to reduce the occurrence of pressure ulcers, there is still room for improvement. Thus there remains a need for further contributions in this area.

SUMMARY

The present disclosure includes one or more of the features recited in the appended claims and/or the following features which, alone or in any combination, may comprise patentable subject matter.

A person support surface may include at least one inflatable bladder, a cover including a portion above the at least one inflatable bladder, and a control system. The control system may include a plurality of sensors that generate data signals indicative of a characteristic of the at least one inflatable bladder and a person's tissue contacting the cover and a processor operatively coupled to the plurality of sensors. The processor may be configured to execute operating logic to determine a surface performance index as a function of the data signals. The control system may have a fluid supply coupled to the at least one inflatable bladder. The processor may control the operation of the fluid supply as a function of the surface performance index.

The control system may be coupled to an electronic medical record (EMR) over a network and may receive information from the EMR for use by the processor in controlling the operation of the fluid supply. The information from the EMR may include a Braden score, pressure ulcer history, superficial lesion history, height, weight, and/or an identification of the person's medication. The control system may alert a caregiver if the fluid supply is unable to be operated to achieve the surface performance index.

The surface performance index may be a function of interface pressure, shear, and temperature. The control system may receive information regarding ambient conditions proximate the person support surface and the control system may modify the contributions of interface pressure, shear, and temperature to the surface performance index as a function of the information regarding the ambient conditions. In some instances, the processor may use a look up table to determine the surface performance index. In other instances, the processor may use the following equation to determine the surface performance index:

$$\text{Surface\_Performance\_Index\_} = \left[\frac{\left(\frac{SPL_1}{SPL_{unloaded}}\right)}{\left(\frac{DMD_1}{DMD_{unloaded}}\right)}\right] = $$

$$\frac{\left[1.00 - \left[\frac{P_1^2 + S_1^2}{P_{occlusion}^2}\right]^{1/2}\right]}{(1 + \%\_\text{reduction\_in\_tissue\_demand})^{\left(\left(\frac{tissue\_temp.\_°C.}{\frac{W}{m^2}}\right)*THW+37.78\right)}}$$

The control system may be configured to adjust at least one of an operating parameter and characteristic of a therapy delivered by the fluid supply via the at least one inflatable bladder. The therapy may comprise, for example, at least one of low air loss therapy, percussion vibration therapy, and continuous lateral rotation therapy.

The at least one inflatable air bladder may include a plurality of inflatable air bladder that are grouped into zones, each zone being inflated by the fluid supply so as to achieve different surface performance indexes. The control system may operate to adjust a first pressure in the at least one air bladder to a second pressure. The second pressure may be configured to lower the combined score $(P^2+S^2)^{1/2}$ in which P corresponds to a pressure measurement and S corresponds to a shear measurement.

At least one of a temperature, humidity, and flow rate of the fluid supplied by the fluid supply may be adjustable. In some embodiments, at least two or all three of a temperature, humidity, and flow rate of the fluid supplied by the fluid supply may be adjustable. The plurality of sensors may include a pressure sensor, a shear sensor and a temperature sensor. In some embodiments, the plurality of sensors may further include a humidity sensor. The at least one bladder may include a topper that extends over substantially an entire length and width of the person support surface.

Some embodiments include a control system for a person support system that may be configured to receive a first set of input signals from an electronic medical record (EMR), generate a surface performance index as a function of interface pressure (P), shear (S), and temperature (T) based on the first set of inputs, receive a second set of input signals from the EMR, determine if the relative contributions of P, S, and/or T should be modified based on the second set of input signals while maintaining the performance index, and regulate a fluid supply as a function of P, S, and T.

In some embodiments a control system for a person support system may be configured to receive a first set of input signals from an EMR, establish thresholds for interface pressure (P), shear (S), and temperature (T) based on the first set of inputs, receive a second set of input signals from a plurality of sensors corresponding to at least one of the bladder pressure, interface pressure, shear, temperature, and/or relative humidity of the tissue and/or person contacting surface, compare the sensed values with the corresponding thresholds, and regulate a fluid supply as a function of difference between the sensed P, S, and T values and the corresponding thresholds.

According to some embodiments, a control system for a person support system may be configured to receive a set of input signals from a plurality of sensors corresponding to the relative humidity of the tissue and/or person contacting surface, look up the value of the relative humidity in a table to determine desired surface performance characteristics, and regulate a fluid supply as a function of surface performance characteristics.

Additional features, which alone or in combination with any other feature(s), such as those listed above and/or those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

Referring now to the illustrative examples in the drawings, wherein like numerals represent the same or similar elements throughout.

DETAILED DESCRIPTION

While the present disclosure can take many different forms, for the purpose of promoting an understanding of the principles of the disclosure, reference will now be made to the embodiments illustrated in the drawings, and specific language will be used to describe the same. No limitation of the scope of the disclosure is thereby intended. Various alterations, further modifications of the described embodiments, and any further applications of the principles of the disclosure, as described herein, are contemplated.

According to some embodiments of the present disclosure, a control system for a person support system is configured to receive a first set of input signals from an electronic medical record (EMR), generate a surface performance index as a function of interface pressure (P), shear (S), and temperature (T) based on the first set of inputs, receive a second set of input signals from the EMR, determine if the relative contributions of P, S, and/or T should be modified based on the second set of input signals while maintaining the performance index, and regulate a fluid supply as a function of P, S, and T.

Alternatively or additionally according to this disclosure, a control system for a person support system is configured to receive a first set of input signals from an EMR, establish thresholds for interface pressure (P), shear (S), and temperature (T) based on the first set of inputs, receive a second set of input signals from a plurality of sensors corresponding to at least one of the bladder pressure, interface pressure, shear, temperature, and/or relative humidity of the tissue and/or person contacting surface, compare the sensed values with the corresponding thresholds, and regulate a fluid supply as a function of difference between the sensed P, S, and T values and the corresponding thresholds.

Further alternatively or additionally according to this disclosure, Yet a control system for a person support system is configured to receive a set of input signals from a plurality of sensors corresponding to the relative humidity of the tissue and/or person contacting surface, look up the value of the relative humidity in a table to determine desired surface performance characteristics, and regulate a fluid supply as a function of surface performance characteristics.

Pressure ulcers sometimes form in areas where a person's tissue is under stress. Several factors have been identified as contributing to tissue break down. Some of the more widely accepted factors include mechanical stresses within the tissue, such as, compression, stretching and distortion of tissue caused by pressure and shear forces. Other factors, such as friction, body heat and moisture have also been identified as contributing to tissue break down. Traditionally, pressure ulcers were thought to result from a single breakdown mechanism: interface pressure and shear force. However, recent studies suggest that wounds generally identified as pressure ulcers can be broken down into different types of wounds resulting from at least two breakdown mechanisms. The first type can be a superficial lesion, which some studies suggest may not be the result of pressure at all and may never progress to deeper tissue layers. These superficial lesions are generally the result of moisture and/or friction, often in combination with other chemical or bacterial irritants. The second type of pressure ulcer is of a type which a growing body of evidence strongly suggests is the result of deep tissue injury (DTI), driven by tissue deformation and ischemia in the skin and underlying areas of muscle and fat. There is some evidence that suggests that, at very high levels of pressure and shear, damage from the deformation alone can be the primary mechanism of damage, independent of the ischemic process. At more moderate levels of stress, such as is sometimes imposed by a support surface, the primary cause of breakdown is generally believed to be ischemia.

Pressure, shear, and temperature have well-defined and quantifiable roles in the ischemic breakdown process, but there is currently no clear-cut, quantifiable connection between skin moisture and ischemia or friction and ischemia. However, this does suggest that the reduction in tissue oxygen levels caused by a surface, which drives ischemic breakdown, could be viewed as a single function of pressure, shear, and temperature. According to this disclosure, this function is derived analytically with the analytical relationship between interface pressure (P), shear (S), and reduction in $tcpO_2$ defined by the following equation:

$$\text{reduction\_in\_}tcpO_2 = \sqrt{(P^2 + S^2)}$$

If the pressure at which perfusion can fully occluded ($P_{occlusion}$) is examined, then the proportional reduction in blood supply to a tissue at a pressure P1 and a shear S1 can be expressed as:

$$\text{proportional\_reduction\_in\_}O_2 = 1.00 - \left[\frac{P_1^2 + S_1^2}{P_{occlusion}^2}\right]^{1/2}$$

In this expression, the denominator is representative of the total tissue mechanical stress at any combination of pressure P1 and shear S1 that cause full occlusion. The numerator represents the total tissue mechanical stress under any set of arbitrary loading conditions. The expression can also be expressed in terms of the supply SPL of blood to the tissue as follows:

$$\frac{SPL_1}{SPL_{unloaded}} = 1.00 - \left[\frac{P_1^2 + S_1^2}{P_{occlusion}^2}\right]^{1/2}$$

Tissue demand for oxygen is reduced by approximately 6-13% per 1° C. that the tissue is cooled. The effect of altering the tissue temperature between two arbitrary temperatures To and T1 can be expressed as follows:

$$\frac{\text{Demand\_for\_O}_2\_\text{at\_T}_1}{\text{Demand\_for\_O}_2\_\text{at\_T}_0} =$$

$$\frac{DMD_{T_1}}{DMD_{T_0}} = (1 + \%\_\text{reduction\_in\_tissue\_demand})^{(T_0 - T_1)}$$

Tissue demand for oxygen can also be expressed as a function of the cooling power of surfaces in terms of total heat withdrawal (THW) rather than tissue temperature. According to this disclosure, the relationship between tissue temperature and total heat withdrawal can be expressed as follows:

$$\text{Tissue\_Temp} = \left(\frac{\text{tissue\_temp.}\_°F.}{\frac{W}{m^2}}\right) * THW + 100 = \left(\frac{\text{tissue\_temp.}\_°C.}{\frac{W}{m^2}}\right) * THW + 37.78$$

Given the previous equation, the effect of temperature on tissue demand for oxygen relative to demand in an uncovered, thermoneutral state can be expressed as follows:

$$\frac{DMD_{T_1}}{DMD_{T_0}} = (1 + \%\_\text{reduction\_in\_tissue\_demand})^{\left(\left(\frac{\text{tissue\_temp.}\_°C.}{\frac{W}{m^2}}\right)*THW+37.78\right)}$$

Generally, when the tissue is unloaded, the supply of oxygen and demand for oxygen is approximately equal, i.e., there generally is no net accumulation or removal of oxygen in the tissue or subcutaneous tissue layers. According to this disclosure, to assess the performance of a person support surface, the unloaded supply and unloaded demand values are compared to the measured supply and measured demand values as shown in the following equation:

$$\text{Surface\_Performance\_Index} = \left[\frac{\left(\frac{SPL_1}{SPL_{unloaded}}\right)}{\left(\frac{DMD_1}{DMD_{unloaded}}\right)}\right] =$$

$$\frac{\left[1.00 - \left[\frac{P_1^2 + S_1^2}{P_{occlusion}^2}\right]^{1/2}\right]}{(1 + \%\_\text{reduction\_in\_tissue\_demand})^{\left(\left(\frac{\text{tissue\_temp.}\_°C.}{\frac{W}{m^2}}\right)*THW+37.78\right)}}$$

The higher the ratio, the greater the likelihood that the surface helps prevent pressure ulcers and/or superficial lesions from developing.

According to some embodiments of this disclosure, the multiple performance indices are plotted in an N-dimensional visualization space and are analyzed using statistical methods to generate equations that provide a fit for the performance indices. In some embodiments, the performance indices are plotted in a 2-dimensional visualization space and/or analyzed using multiple variable regression techniques. In other embodiments, a table is generated containing the multiple surface performance indices with corresponding values of interface pressure, shear force, and temperature. The table is used as a look-up table. An example of a look-up table having surface performance index values calculated according to this disclosure is provided as follows:

TABLE 1

Support Surface Performance Table

|  | Pressure (mm Hg) | Shear (mm Hg) | THW (W/sq. m) | Performance Index (SPL/DMD) |
|---|---|---|---|---|
| Surface A | 32 | 0.6 | 250 | 0.97 |
| Surface B | 47 | 2.2 | 87 | 0.40 |
| Surface C | 51 | 2.2 | 70 | 0.33 |
| Surface D | 52.5 | 3.2 | 62 | 0.31 |
| Surface E | 51 | 3.2 | 10 | 0.28 |
| Surface F | 56.5 | 2.9 | 53 | 0.26 |
| Surface G | 57 | 3.6 | 27 | 0.23 |
| Surface H | 70 | 4 | 12 | 0.05 |

It is contemplated by this disclosure that one or both of the analytical model and the statistical model is used, as desired, in ranking and/or controlling one or more functions of person support systems.

Figure 1:
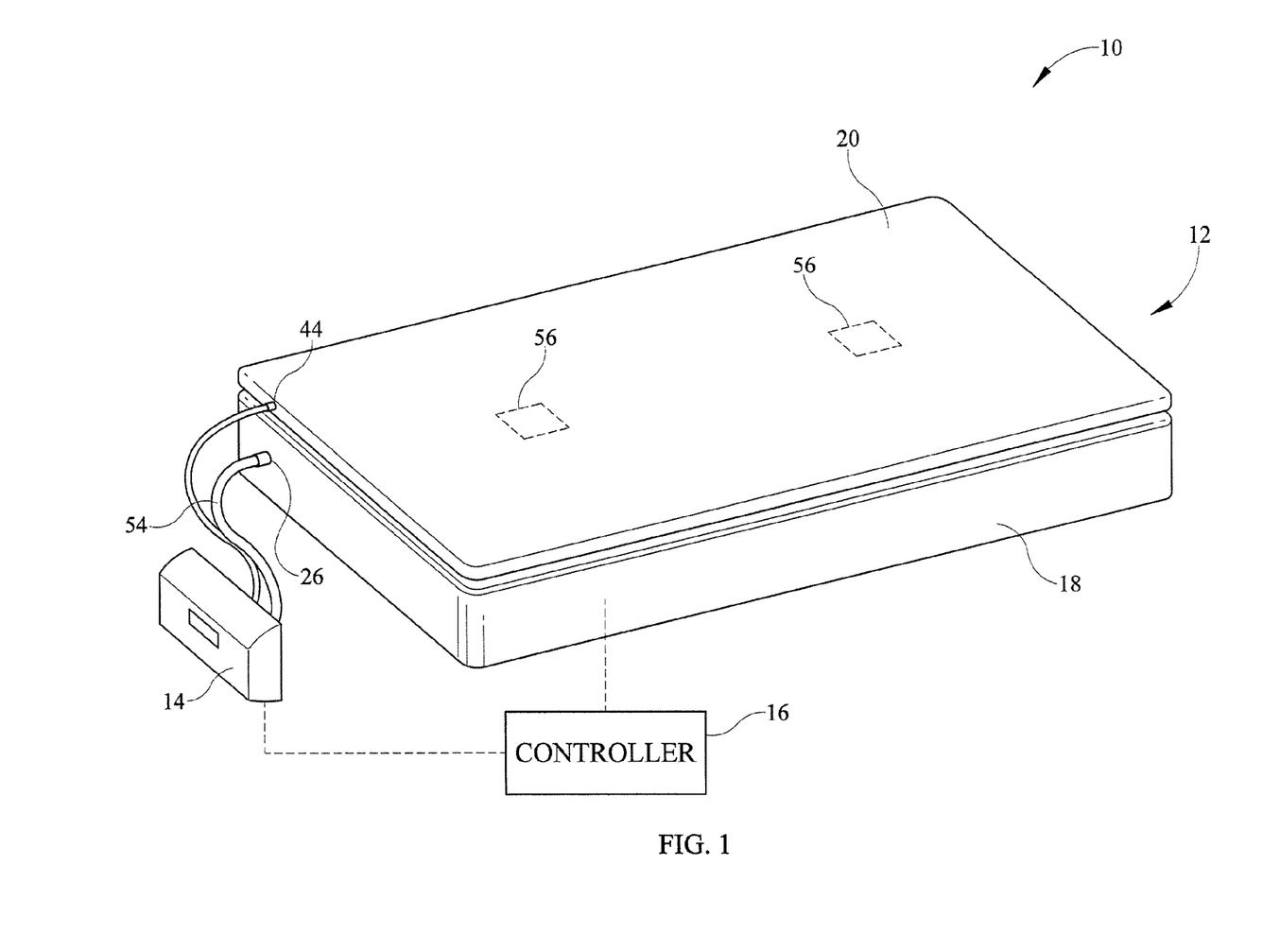
FIG. 1 is a perspective view of a person support system according to one illustrative embodiment.

A person support system 10 suitable for being controlled according to one or both of the analytical model and the statistical model is shown in FIG. 1. The person support system 10 includes a person support surface 12, a fluid supply 14, and a control system 16. In some instances, the person support system 10 is used in the hospital setting and is supported on a person support apparatus (not shown), such as a hospital bed, stretcher, or other support structure. If desired, the person support system 10 can be supported on a floor (not shown), although typically, that is not intended to be the most common arrangement. The person support system 10 is configured to help reduce the likelihood of developing pressure ulcers and/or superficial lesions by maintaining at least one of the interface pressure, temperature, moisture, shear force, and/or friction within predetermined ranges.

Figure 2:
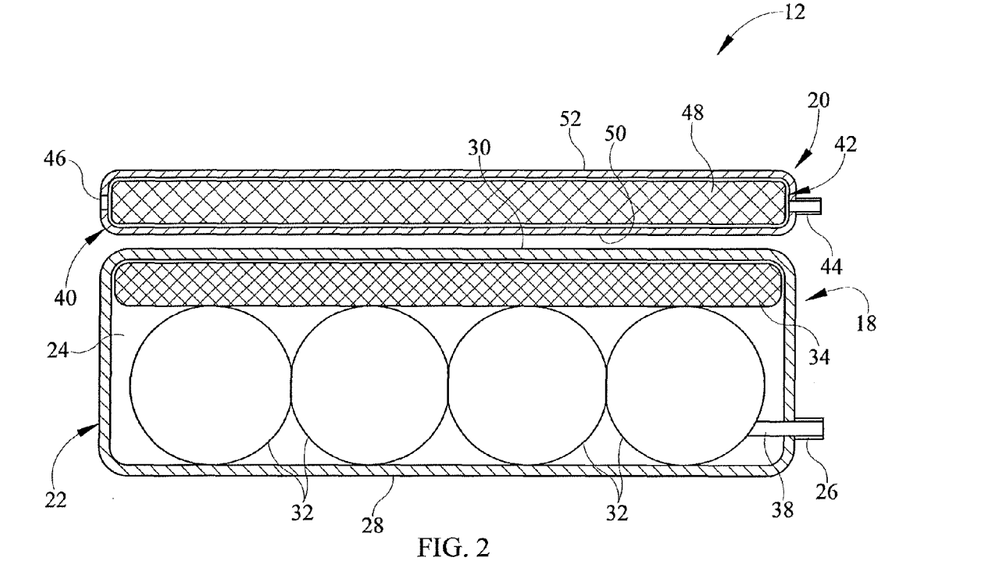
FIG. 2 is a cross-sectional view of a mattress and a topper of the person support system of FIG. 1 taken laterally across a width of the mattress and topper.
Figure 3:
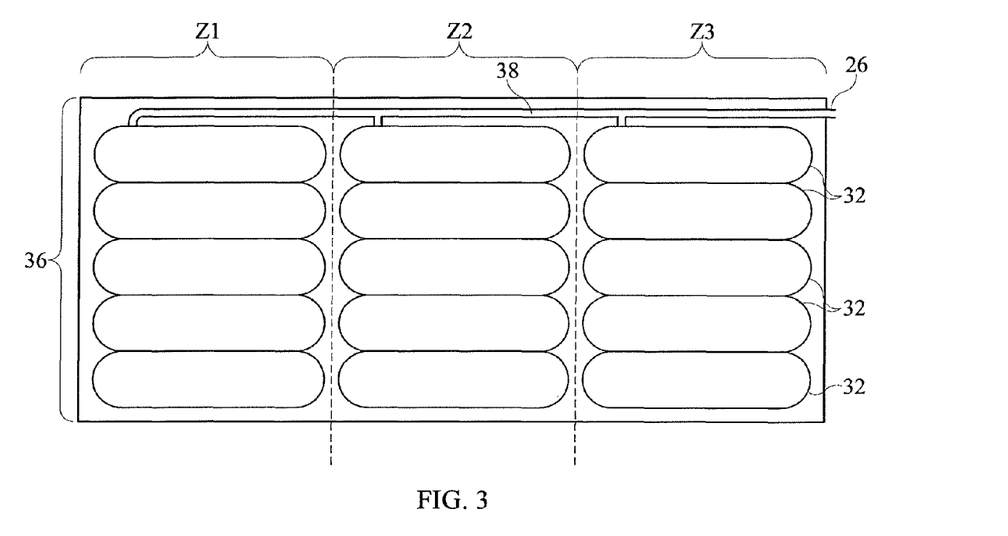
FIG. 3 is a diagrammatic top view of the mattress of FIG. 2 inflatable air bladders forming three support zones according to this disclosure.

The person support surface 12 is configured to support a person thereon. In some embodiments, the person support surface 12 includes a mattress 18 and a mattress topper 20 as shown in FIGS. 1 and 2. In some embodiments, the mattress topper 20 is integrated into the mattress 18. That is, the mattress 18 and topper 20 are coupled together to form a support surface unit in some embodiments. In other embodiments, the mattress 18 is provided without the mattress topper 20. The mattress 18 in the illustrative example has multiple zones, such as, a first zone Z1 or head zone Z1, a second zone Z2 or seat zone Z2, and a third zone Z3 or foot zone Z3 as shown in FIG. 3. In some embodiments, the zones Z1-Z3 are independently controlled by the fluid supply 14.

The mattress 18 includes an outer mattress cover 22 or mattress ticking 22 that envelopes an area to define a mattress chamber 24, and a mattress inlet 26 as shown in FIG. 2. The mattress ticking 22 has a support contacting surface 28 that contacts the person support apparatus (or floor), and a topper contacting surface 30 that interfaces with the mattress topper 20. In some embodiments, the topper contacting surface 30 serves as a person contacting surface 30 where the mattress topper 20 is integrated into the mattress 18, or the person support surface 12 does not include a mattress topper 20. The mattress ticking 22 is composed of a urethane and/or polytetrafluoroethylene (PTFE) coated nylons or other fabrics, for example. It is contemplated by this disclosure that the mattress ticking 22 can be made of other materials, such as those that are configured to prevent water from passing therethrough while allowing vapor to be transmitted therethrough.

The mattress chamber 24 contains a plurality of fluid bladders 32 and a mattress spacer 34 therein as shown in FIG. 2. In some embodiments, the mattress 18 contains only one mattress bladder 32 within the mattress chamber 24. In some embodiments, the mattress 18 is made of a polymeric material, such as, foam, foam blocks, foam layers of varying density, and/or include foam borders, which are used in combination with fluid bladders 32 in some embodiments, which fluid bladders themselves may or may not have internal foam. In some embodiments, the bladders 32 and/or topper 20 provide therapy and/or low air loss functionality through varying air pressure, blowing air, or exhausting air. In some embodiments, the fluid bladders 32 are gas bladders 32 that are alternately inflated and deflated and the mattress spacer 34 is made of foam and positioned between the fluid bladders 32 and the mattress ticking 22. The bladders 32 are arranged to form bladder arrays 36 that are positioned adjacent one another and/or on top of one another with the bladders 32 in the same or a different orientation. In some embodiments, the bladders 32 and/or bladder arrays 36 are in communication with one another such that the fluid pressure in the bladders 32 and/or bladder arrays 36 is maintained as pressure is exerted on the bladders 32 and/or bladder arrays 36, e.g., supporting a person thereon. In some embodiments, the bladders 32 or bladder arrays 36 are connected together with a connector 38 that couples the bladders to the mattress inlet 26.

The bladders 32 and/or bladder arrays 36 are configured, in some instances, to deliver therapy to a person supported on the person support surface 12. In some embodiments, the bladders 32 and/or bladder arrays 36 deliver therapy through sequential pressure increases/decreases and/or rapid changes in pressure of the bladders 32 and/or bladder arrays 36 as shown in FIG. 3. For example, one or more sections of the surface 18 may provide alternating pressure therapy, continuous lateral rotation therapy, boost assistance, percussion/vibration therapy, and/or turn assistance. In some embodiments, the bladders 32 and/or bladder arrays 36 exhaust gas into the mattress chamber 24.

Figure 4:
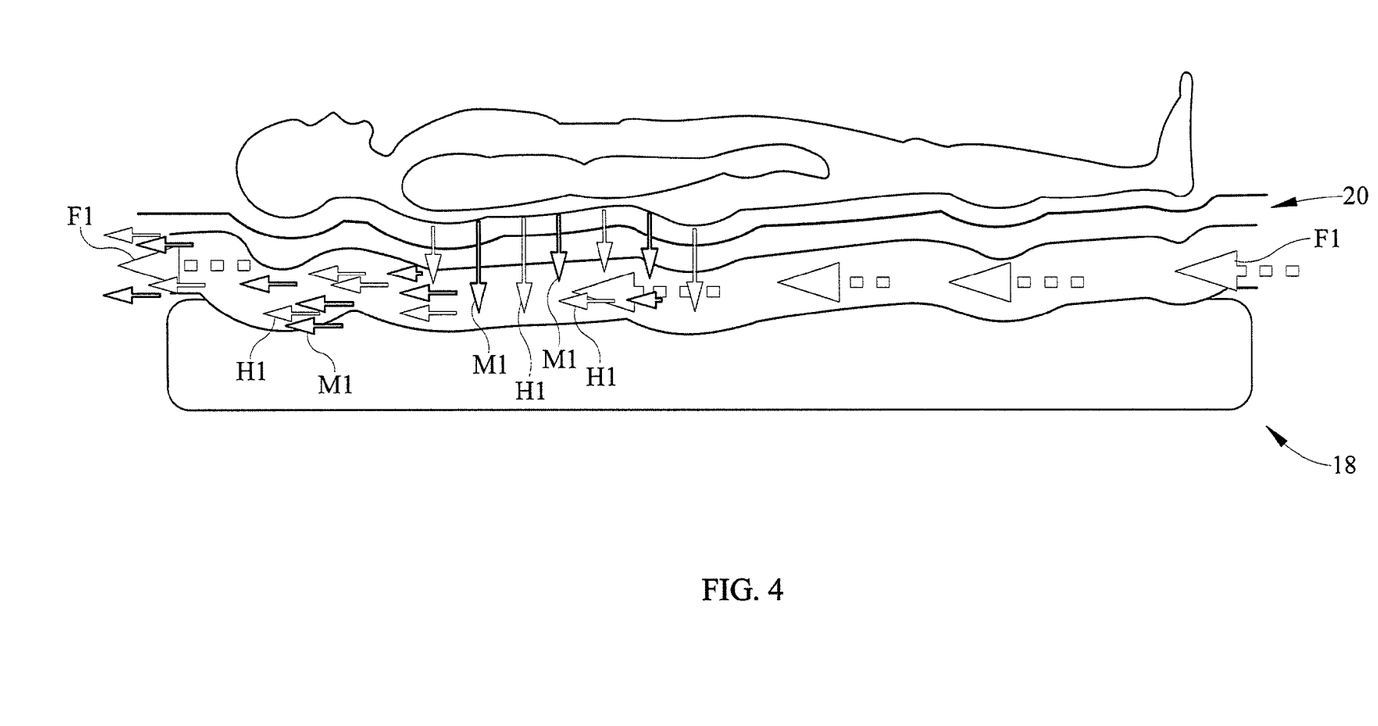
FIG. 4 is diagrammatic side view of the mattress and the topper of FIG. 2 showing a flow of air, moisture, and heat with respect to the mattress and the topper.

The mattress topper 20 is coupled to the mattress 18 and interfaces with the person supported on the person support surface 12 in some embodiments as shown in FIG. 4. In some embodiments, the mattress topper 20 is a low air loss topper 20. Low air-loss broadly refers to a feature of a support surface that provides a flow of air to assist in managing the heat and humidity (microclimate) of the tissue contacting a surface. There are two types of mechanisms that low air-loss support devices typically use to remove accumulated moisture and heat: convective evaporation and diffusive evaporation. Convective evaporation evaporates accumulated moisture by blowing air on the tissue. Diffusive evaporation evaporates accumulated moisture through and under the surface of the support device to cool the tissue without blowing air directly on the tissue. An example of a diffusive device is shown in FIG. 4 in which a person is lying on the support surface 12 in the supine position with fluid F1 flowing through the support surface 12 to remove heat H1 and moisture M1 radiated by the person. In some low air-loss support devices contemplated by this disclosure, a combination of diffusive and convective evaporation is used.

The mattress topper 20 includes a topper cover 40 or ticking 40 that defines a topper chamber 42, a topper inlet 44, a topper vent 46, and a spacer 48 as shown in FIG. 3. The topper ticking 40 includes a mattress contacting surface 50 and a person contacting surface 52. The mattress contacting surface 50 interfaces with the topper contacting surface 30. The person contacting surface 52 interfaces with a person lying thereon. The mattress contacting surface 50 and the patient contacting surface 52 are generally shaped to cooperate with the topper contacting surface 30 and are secured to one another along their respective edges by ultrasonic welding, for example, in order to form a substantially fluid-tight seal. Alternatively or additionally, the mattress contacting surface 50 and the patient contacting surface 52 are secured to one another by adhesive, plastic welding, or other securing means, and are secured along various portions of the mattress contacting surface 50 and the patient contacting surface 52.

In one illustrative embodiment, the ticking 50 is vapor permeable and impermeable to both liquids and air. It is within the scope of this disclosure for the ticking 50 to be both vapor permeable and air permeable. In some embodiments, the mattress ticking 22 and the ticking 50 are made of the same material and have the same physical characteristics.

The inlet 44 is positioned along a side of the topper 20 and allows for fluid to be communicated from the control system 14 into the chamber 42 in the illustrative example as shown in FIGS. 2 and 3. The inlet 44 includes an inlet coupler that couples the control system 14 to the topper 20 such that there is a substantially fluid-tight seal between the inlet 44 and the topper 20.

The vent 46 or outlet 46 is positioned along a side of the topper 20 opposite the inlet 44 in the illustrative embodiment as shown in FIG. 2. The vent 46 allows fluid entering the inlet 44 and passing through the chamber 42 to exit the topper 20.

The spacer 48 is positioned within the chamber 42 and separates the mattress contacting surface 50 from the patient contacting surface 52 as shown in FIG. 2. It is contemplated that, in some embodiments, the spacer 48 is made of material(s) having a high fluid porosity and having some resistance against flattening, while not being so stiff as to increase interface pressure too dramatically. In some embodiments, the spacer 32 includes at least one bladder (not shown). In some embodiments, the mattress spacer 34 and the spacer 48 are made of a similar material and/or have similar physical characteristics. The thickness of the spacer 48 is between about 0.1" and 0.75" in some embodiments. It should be appreciated that the thickness of the spacer 48 can be greater than 0.75" if desired.

The fluid supply 14 is configured to supply fluid to the bladders 32, bladder arrays 36, and/or the mattress topper 20 as shown in FIG. 1. In some embodiments, there are multiple fluid supplies 14, with a first fluid supply supplying fluid to the bladders 32 or bladder arrays 36 and a second fluid supply 32 supplying fluid to the mattress topper 20. In some embodiments, the fluid supplies 14 include a gas blower 14 that supplies air to the bladders 32, bladder arrays 36, and/or the mattress topper 20. It is within the scope of this disclosure for the fluid supply 14 to supply various other gasses and/or liquids rather than air. In some embodiments, the fluid supply 14 is integrated into the mattress 16. In other embodiments, the fluid supply 14 is coupled to a person support apparatus or supported on other supporting structures. The fluid supply 14 supplies the fluid through a connector 54 to the inlet 26 of the mattress 16 and/or the inlet 44 of the mattress cover 20 in the illustrative example. In some embodiments, the fluid supply 14 is removably coupled to the inlet 26 of the mattress 16 and/or the inlet 44 of the mattress cover 20 through a hose 54. Optionally, the fluid supply 14 includes a heating/cooling element (not shown) that can heat/cool the fluid being supplied.

Figure 5:
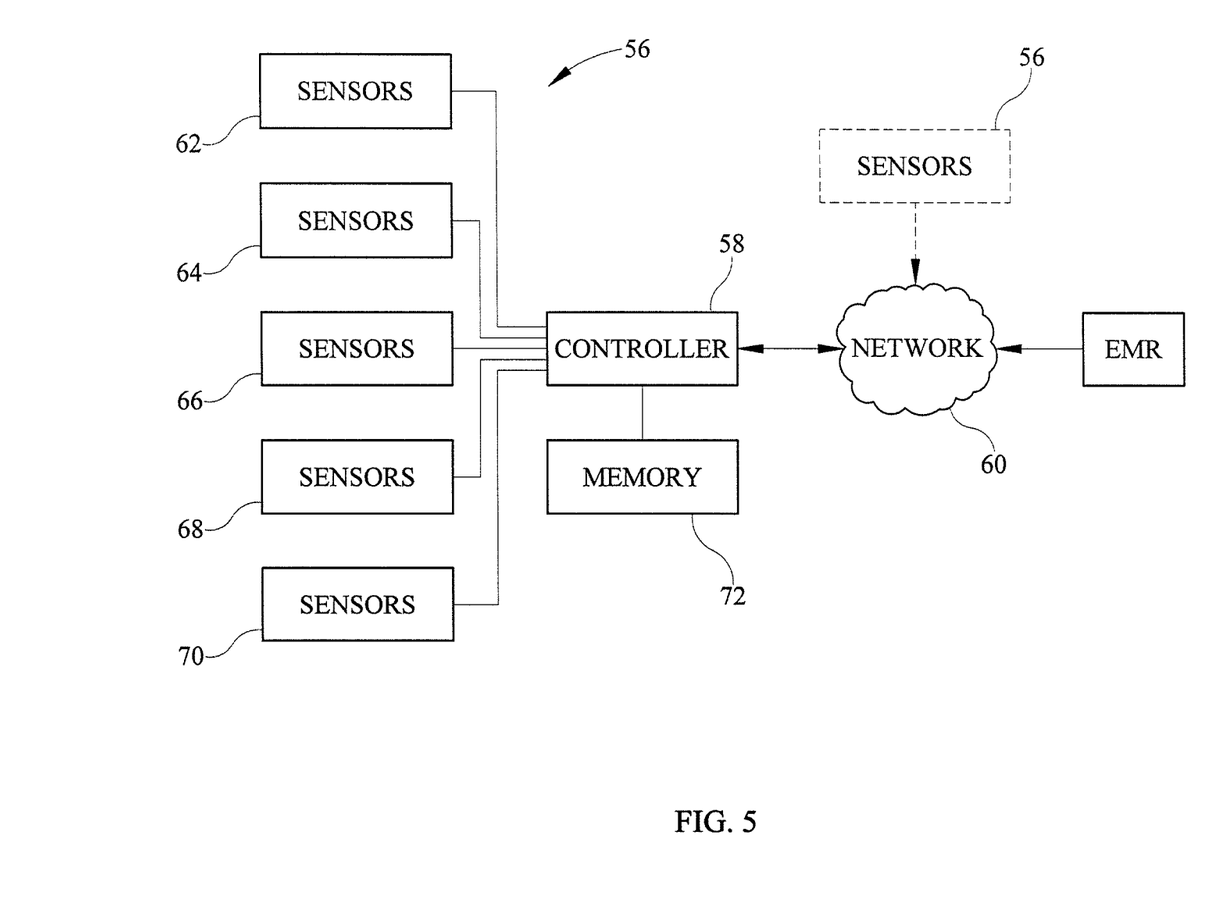
FIG. 5 is diagrammatic view of a control system of the person support system of FIG. 1 according to this disclosure.

The control system 16 for person support system 10 includes a plurality of sensors 56 and a controller 58 operatively coupled to the fluid supply 14 and the plurality of sensors 56 as shown in FIGS. 1 and 5. The control system 16 is configured to control various functions of the person support surface 12, such as, administering therapy to a person supported on the person support surface 12. In some embodiments, the control system 16 is configured to communicate information about the person support system 10 over a hospital network (not shown) and/or alert caregivers. At least a portion of the control system 16 is integrated into and/or coupled to the support surface 12 in some embodiments. For example, the fluid supply 14, the plurality of sensors 56, and the controller 58 are all incorporated within the person support surface 12 in some instances.

The sensors 56 are operatively coupled to the controller 58 and are configured to sense various parameters, including, but not limited to, a temperature of a tissue and/or the person contacting surface 52, a relative humidity of the interface between a tissue and the person contacting surface 52, an amount of shear between the person contacting surface 52 and the tissue, and a pressure of the fluid inside the bladders 32. In some embodiments, the sensors 56 and the controller 58 are coupled to a network 60 and the controller 58 receives data signals from the sensors 56 over the network 60. In some embodiments, the sensors 56 include temperature sensors 62 integrated into the person contacting surface 52 and configured to sense the temperature of a tissue contacting the person contacting surface 52. Alternatively of additionally, the sensors 56 include moisture sensors 64 integrated into the person contacting surface and configured to sense the relative humidity of the interface between a tissue and the person contacting surface 52.

Further alternatively or additionally, the sensors 56 include shear sensors 66 integrated into the person contacting surface 52 and configured to sense the amount of shear between the person contacting surface 52 and the tissue. Still further alternatively or additionally, the sensors 56 include bladder pressure sensors 68 positioned within the bladders 32 or between adjacent bladders 32 and configured to sense the fluid pressure within the bladders 32. Optionally, one or more of the sensors 56 comprise interface pressure sensors 70 integrated into the person contacting surface 52 and configured to sense the interface pressure between the tissue and the person contacting surface 52 by measuring the amount of force on the person contacting surface 52. In some embodiments, the sensors 56 include sensors configured to sense environmental conditions, such as, ambient temperature and humidity. In some embodiments, the sensors 56 are integrated into the ticking 40 by being coupled to the ticking via a suitable coupler such as adhesive or via lamination, for example. In other embodiments, the sensors 56 are situated adjacent the ticking 40.

The sensors 56 are configured to generate analog and/or digital signals. In some embodiments, the sensors 56 generate an analog data signal and are connected directly to the controller 58 as shown in FIG. 5. In other embodiments, the sensors 56 are configured to produce a digital data signal, e.g., a serial digital data signal, and can be connected to the network 60, e.g., a Serial Peripheral Interface (SPI) network, to communicate with the controller 58 if desired.

The controller 58 is configured to regulate the fluid supply 14 to control various characteristics of the person support surface 12 in response to data signals received from the sensors 56 and/or from a person's electronic medical record (EMR). In some embodiments, the EMR is copied and stored locally on the controller 58 or in a memory location coupled to the network 60. In some embodiments, the controller 58 is configured to regulate the fluid supply 14 in accordance with parameters identified in a look-up table using the data signals from the sensors 56. Alternatively or additionally, the controller 58 is configured to regulate the fluid supply 14 as a function of the data signals from the sensors 56. In some embodiments, the controller 58 is configured to regulate the fluid supply 14 with parameters identified in a look-up table using information from the EMR of a person supported on the person support surface 12. In still other contemplated embodiments, the controller 58 is configured to regulate the fluid supply 14 in accordance with both the data signals and the EMR information. Alternatively or additionally, the controller 58 is configured to regulate the fluid supply 14 in accordance with a user input.

The controller 58 can be located in a variety of places. In some embodiments, the controller 58 is incorporated into a graphical user interface (not shown) and is configured to receive user inputs, e.g., from a caregiver and/or person supported on the person support apparatus. It is contemplated by this disclosure that the graphical user interface is coupled to the person support apparatus or support structure or equipment management system. In other embodiments, the controller 58 is integrated into an external network (not shown), such as a hospital network. In some embodiments, the controller 58 is integrated into the fluid supply 14.

The controller 58 includes memory 72, shown in FIG. 5, and stores data signals received from the sensors 56 in the memory 72 in some embodiments. In other embodiments, the memory 72 is separate from the controller 58. Alternatively or additionally, the controller 58 receives one or more user input signals from a user input device (not shown) that allows the person (caregiver and/or person supported on the person support system 10) to influence the regulation of the fluid supply 14. In some embodiments, the user input signal(s) is only able to influence the regulation of the fluid supply 14 within the predetermined ranges. The controller 58 is configured to execute operating logic 76 that defines various control, management, and/or regulation functions. This operating logic 74 is in the form of software, firmware, and/or dedicated hardware, such as, a series of programmed instructions, code, electronic files, or commands using general purpose or special purpose programming languages or programs executed on one or more general purpose or special purpose computers, processors, other control circuitry, or networks; a hardwired state machine; and/or a different form as would occur to those skilled in the art.

Figure 6:
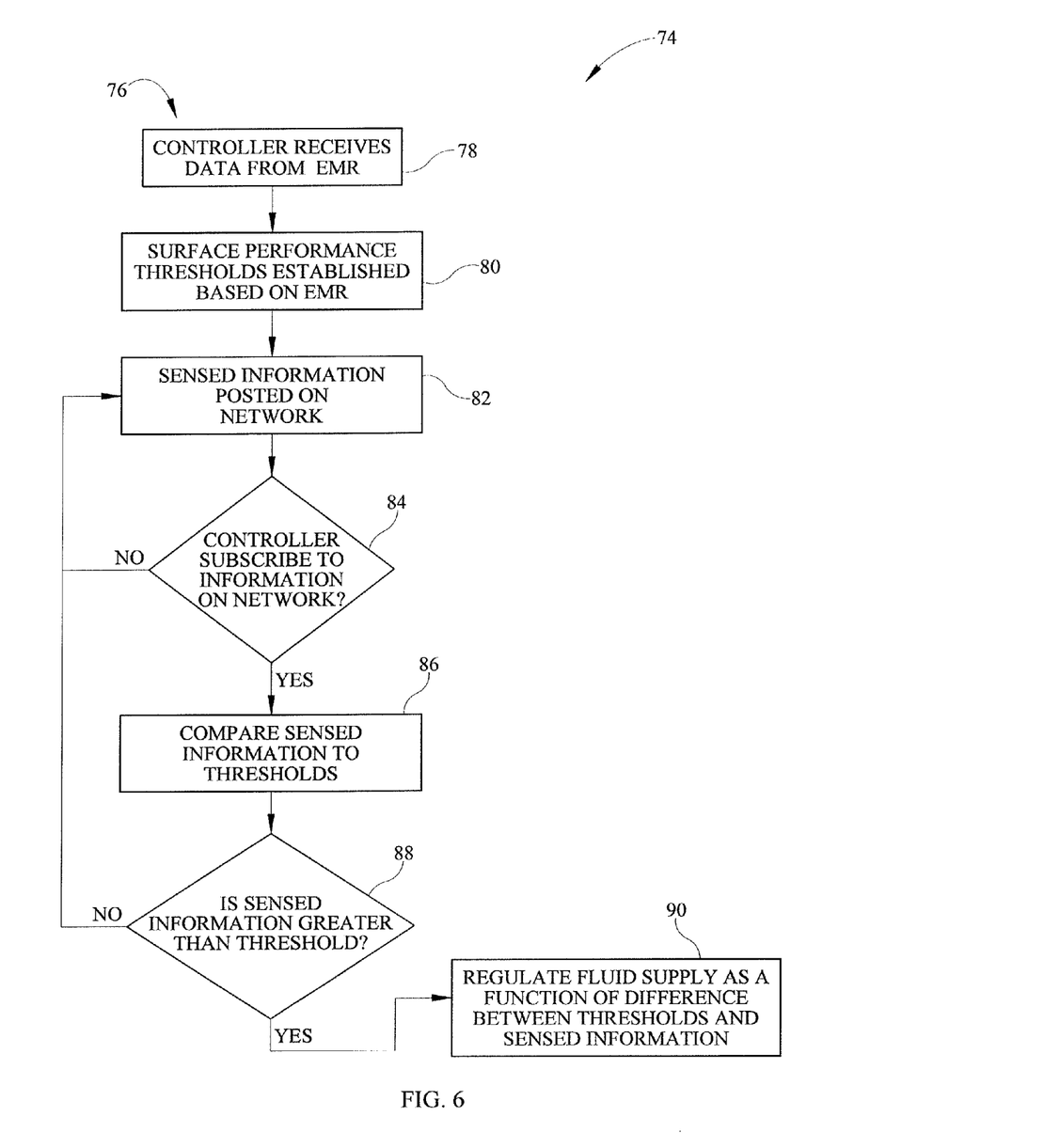
FIG. 6 is a flow chart illustrating one optional procedure executed by the control system of FIG. 5 according to this disclosure.

In some embodiments, the controller 58 includes operating logic 74 in the form of procedure 76 for example, as shown in the flowchart of FIG. 6. Procedure 76 includes operations/ conditionals as indicated at blocks 78, 80, 82, 84, and 86. Procedure 76 is used to regulate the fluid supply 14 as a function of the data signals from the interface pressure sensors 70, the shear force sensors 66, and the temperature sensors 62.

Procedure 76 begins with the operation of block 78 wherein the controller 58 receives data from the EMR which data is indicative of the person's susceptibility to developing pressure ulcers and/or superficial lesions. The EMR data includes, for example, a person's height, weight, pressure ulcer history, superficial lesion history, medications being administered, medical conditions, skin condition, and/or resistance to friction and shear tearing forces. For example, medications like Pamelor for depression or Pylocarpine for Glaucoma may cause a person to sweat at a lower skin temperature. In another example, the medication Prednisone, which is used to combat inflammation, sometimes can significantly reduce the skin's resistance to friction and shear tearing forces. In still another example, medical conditions, such as, diabetes can inhibit a person's ability to sweat and lead to a higher skin temperature.

In the operation of block 80, the controller 58 uses the EMR data to identify standard hospital specific protocols that are, in turn, used to establish threshold values for interface pressure, shear, and temperature for the particular person. In some embodiments, the thresholds are generic pre-programmed thresholds. Alternatively or additionally, the thresholds are input by a user through the user interface and/or a remote location. In some embodiments, threshold values are also established for friction and moisture.

In the operation of block 82, the sensors 56 sense at least one of the interface pressure between the surface and a tissue, the amount of shear between the surface and the tissue, and the temperature of the tissue. In some embodiments, the sensors 56 also sense the moisture between the tissue and the person contacting surface 52. Alternatively or additionally, one or more of the sensors 56 sense environmental conditions, such as, ambient temperature and humidity. The sensors 56 post the sensed information as a value or an event on the network 60 in some embodiments.

In the conditional of block 84, the controller 58 determines if it subscribes to the information on the network 60 and, if it does, it inputs the information into the operating logic 74. For example, the controller 58 will elect to receive the data signal corresponding to the interface pressure, amount of shear, and the temperature in some embodiments. In the operation of block 86, if the controller 58 determines in the conditional of block 84 that the controller 58 subscribes to the information, then the controller 58 compares the sensed information to corresponding threshold values.

In the conditional of block 88, if one or more of the sensed values is greater than the associated threshold value, the controller 58 regulates the fluid supply 14 as a function of the difference between the sensed value and the threshold value in the operation of block 90. In some embodiments, the controller 58 looks up the difference between the threshold and the sensed value in a look-up table to determine the corresponding desirable support surface characteristics and/or support surface performance index. The controller 58 then proceeds to cause the fluid supply 14 to increase/decrease the pressure within the fluid bladders 32 as appropriate. It has been found that increasing the pressure in fluid bladders 32 helps reduce friction and therefore, helps reduce instances of superficial lesions. It has been found that decreasing the pressure in the fluid bladders 32 helps reduce the instances of pressure ulcers. In some embodiments, the controller 58 causes the fluid supply 14 to raise/lower the temperature of the fluid within the fluid bladders 32 and/or flowing through the mattress topper 20. It has been found that lowering the temperature of the fluid flowing through the mattress cover 22 and/or the fluid contained within the fluid bladders 32 helps reduce instances of pressure ulcers and/or superficial lesions. In some embodiments, the controller 58 operates the fluid supply 14 so as to raise or lower the support surface performance index from a previous support surface performance index to a desirable support surface performance index. In some contemplated embodiments, the controller 58 operates the fluid supply 14 to maintain the existing support surface performance index while varying at least one of the interface pressure, shear force, and tissue temperature. In still other embodiments, the controller 58 regulates the fluid supply 14 as a function of the EMR data and the sensor signals. Alternatively or additionally, the controller 58 receives a user input and regulates the fluid supply 14 as a function thereof. In some embodiments, the user input corresponds to a person's comfort level and is allowed to vary the surface performance index by ±5%. In still other embodiments, the controller 58 regulates the fluid supply 14 and the temperature of the fluid from the fluid supply 14 as a function of one or more environmental conditions, such as, ambient temperature and humidity.

Figure 7:
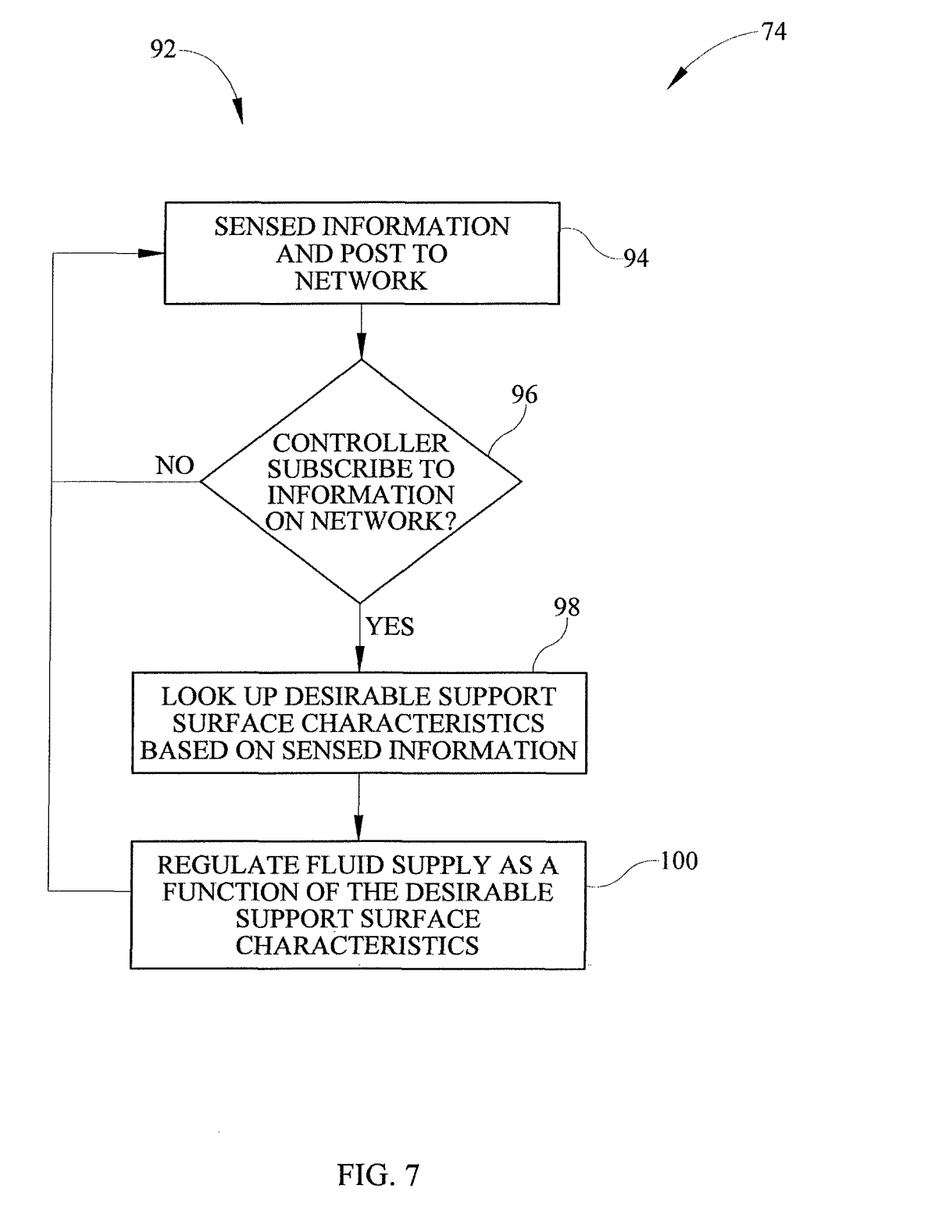
FIG. 7 is a flow chart illustrating a second optional procedure executed by the control system of FIG. 5 according to this disclosure.

In some embodiments, the controller 58 includes operating logic 74 in the form of procedure 92, for example, as shown in the flowchart of FIG. 7. Procedure 92 includes the operations/conditionals of blocks 94, 96, 98, and 100. Procedure 92 is used to regulate the fluid supply 14 as a function of the coefficient of friction of the surface and data signals from the moisture sensors 56 in some embodiments. It is contemplated by this disclosure that the coefficient of friction for the surface is stored in the memory 72. Alternatively or additionally, the coefficient of friction for the surface is entered by a user through a user interface. In some embodiments, the coefficients of friction for multiple surfaces are input into a table and a user (or the controller) selects the coefficient corresponding to the support surface 12 being used.

Procedure 92 begins with the operation of block 94 in which the sensors 56 sense the amount of moisture present at the interface between a tissue and a surface. The sensors 56 post the sensed information as a value or an event on the network 60. In the conditional of block 96, the controller 58 determines if it subscribes to the information on the network 60, and if it does, it inputs the information into the operating logic 74.

In the operation of block 98, if the controller 58 subscribes to the information, then the controller uses the information to determine a desirable set of support surface characteristics. In some embodiments, therefore, the controller 58 receives the data signal corresponding to the amount of moisture and determines a desirable set of support surface characteristics. In some embodiments, the controller 58 looks up the moisture value in a table and the corresponding coefficient of friction to determine the corresponding desirable support surface characteristics and/or support surface performance index. In some embodiments, the controller 58 calculates desirable support surface characteristics and/or support surface performance index as a function of the coefficient of friction and the amount of moisture.

In the operation of block 100 the controller 58 regulates the fluid supply 14 as a function of the desirable support surface characteristics. In some embodiments, the controller 58 operates the fluid supply 14 to increase/decrease the pressure within the fluid bladders 32. Alternatively or additionally, the controller 58 operates the fluid supply 14 to raise/lower the temperature of the fluid within the fluid bladders 32 and/or flowing through the mattress topper 20. Further alternatively or additionally, the controller 58 causes the fluid supply 14 to raise/lower the support surface performance index from a previous support surface performance index to the desirable support surface performance index. In some embodiments, the controller 58 operates the fluid supply 14 to maintain the existing support surface performance index while varying at least one of the amount of moisture (which can be accomplished by varying the temperature of the fluid flowing through the mattress cover 22 and/or the temperature of the fluid in the fluid bladders 32) and the coefficient of friction which can be modified by adjusting the firmness of the bladders 32. In other contemplated embodiments, the controller 58 receives a user input and regulates the fluid supply 14 as a function thereof. It some embodiments, the user input corresponds to a person's comfort level and is allowed to vary the surface performance index by ±5%. In some embodiments, the controller 58 regulates the fluid supply 14 as a function of environmental conditions, such as, ambient temperature and humidity.

Figure 8:
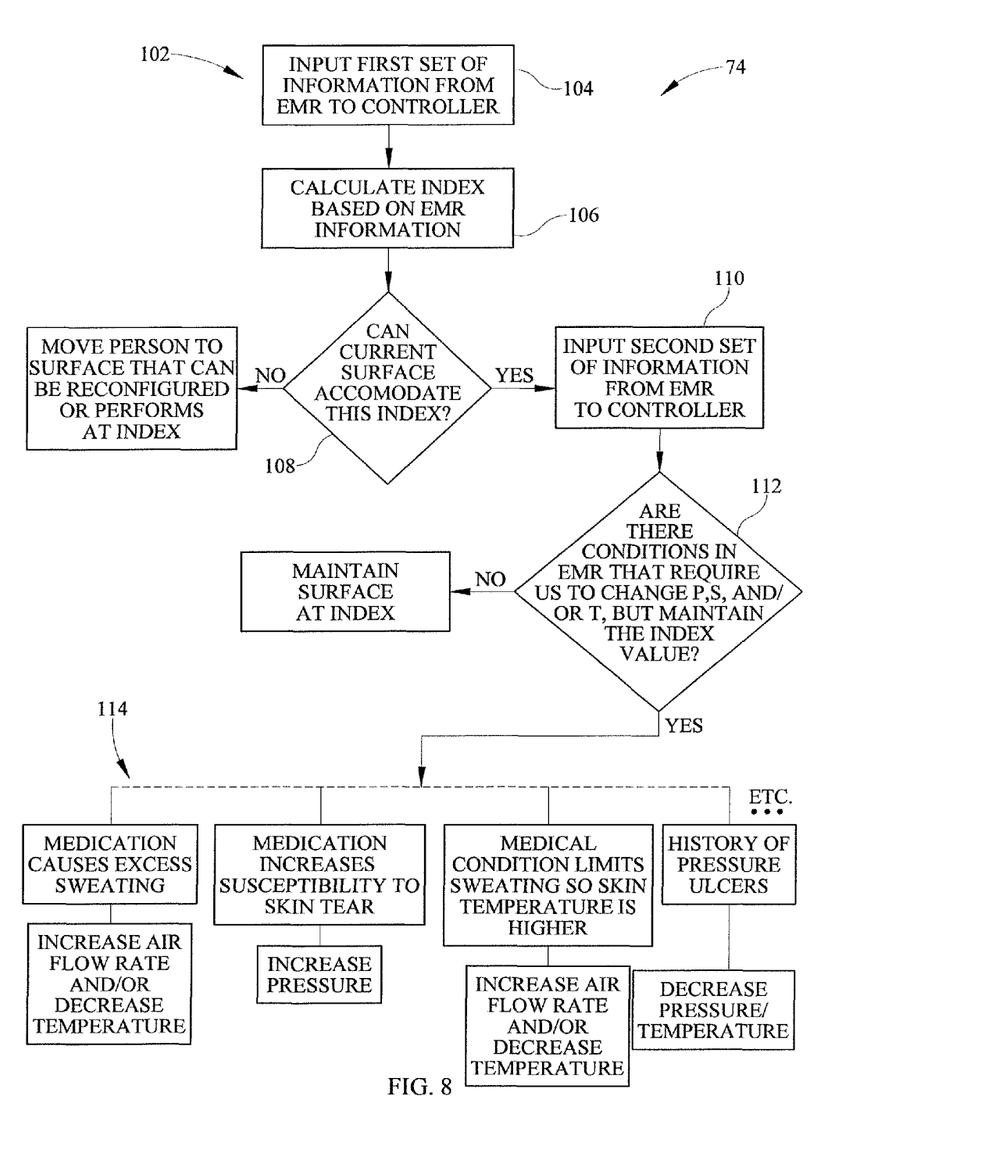
FIG. 8 is a flow chart illustrating a third optional procedure executed by the control system of FIG. 5 according to this disclosure.

In yet other embodiments, the controller 58 includes operating logic 74 in the form of procedure 102, for example, as shown in the flowchart of FIG. 8. Procedure 102 includes the operations/conditionals of blocks 104, 106, 108, 110, 112, and 114. Procedure 102 is used to regulate the fluid supply 14 as a function of data from the EMR of the person supported on the person support surface 12.

Procedure 102 begins with the operation of block 104 in which the controller 58 receives a first set of information from the EMR corresponding to the person's susceptibility to developing pressure ulcers and/or superficial lesions. The first set of EMR information can include information, such as, for example, a Braden risk score, a person's height, weight, pressure ulcer history, superficial lesion history, and other similar information.

In the operation of block 106 the controller 58 uses the first set of EMR information to calculate a surface performance index as a function of interface pressure, shear, and temperature. In some embodiments, the controller 58 looks up the first set of EMR information in a lookup table that identifies support surface characteristics and/or support surface performance indices. In some embodiments, at least some of the values in the table are based on the National Clearinghouse Guidelines. According to some embodiments contemplated by this disclosure, the surfaces are tested to determine the P, S, and T indices for each and then converted to a performance index, which may correspond to a single Braden risk score or range or risk scores, for example. In other embodiments, the controller 58 examines the Braden risk score to determine the level of risk the person is at and then identifies surfaces that have a performance index corresponding to the level of risk. In some embodiments, the controller 58 uses mathematical algorithms to calculate the support surface performance index as a function of interface pressure, shear, and temperature based on the first set of EMR information.

In the conditional of block 108, the controller 58 determines which person support surfaces 12 are appropriate for the person. In some embodiments, the controller 58 outputs the index to a display (not shown) and a caregiver selects the appropriately rated person support surface 12. Alternatively or additionally, the controller 58 outputs a list of person support surfaces 12 rated at or above the index to a display (not shown). In some embodiments, the controller 58 is programmed with a surface identifier that includes a performance index that the person support surface is rated for, and alerts the caregiver, audibly or visually, whether the surface is rated at least one of below the index and greater than or equal to the index. In some embodiments, the controller 58 controls a person support surface 12 to change its initial performance index so that the person support surface 12 is operating at the calculated performance index.

In the operation of block 110, the controller 58 receives a second set of information from the EMR corresponding to the person's medical information. The second set of EMR information includes medical information, such as, for example, a person's medical diagnosis information and/or history, current and/or previous medications, personal preferences, current superficial lesions, current pressure ulcers, and other similar information.

In the conditional of block 112, the controller 58 determines if and by how much the relative contributions of pressure, shear, and temperature should be adjusted based on the second set of EMR information while maintaining the performance index. In one example, medications like Pamelor for depression or Pylocarpine for Glaucoma can cause a person to sweat at a lower skin temperature, which suggests that the flow rate of the fluid from the fluid supply 14 should be increased and/or the temperature reduced. In another example, the medication Prednisone, which can be used to combat inflammation, can significantly reduce the skin's resistance to friction and tearing forces, which suggests that the pressure in the fluid bladders 32 should be increased. In still another example, medical conditions, such as, diabetes can inhibit a person's ability to sweat and lead to a higher skin temperature, which suggests that the flow rate of the fluid from the fluid supply 14 should be increased and/or the temperature should be reduced.

In the operation of blocks 114, the controller 58 further regulates the fluid supply 14 as a function of parameters other than the interface pressure, shear, and temperature values established in operation 110 to maintain the person support surface 12 at the performance index established in operation 106. In some embodiments, the controller 58 causes the fluid supply 14 to increase/decrease the pressure within the fluid bladders 32 based on these other parameters. In some embodiments, the controller 58 causes the fluid supply 14 to raise/lower the temperature of the fluid communicated to the fluid bladders 32 and/or through the mattress topper 20 based on these other parameters. Alternatively or additionally, the controller 58 causes the fluid supply 14 to adjust the bladder 32 pressures and/or the temperature of the fluid in the bladders 32 and/or flowing through the mattress topper 20 to raise/lower the support surface performance index from an initial support surface performance index to the calculated support surface performance index based on these other parameters. In some embodiments, the controller 58 causes the fluid supply 14 to maintain the existing support surface performance index while varying the performance of the fluid supply 14 as a function of at least one of the interface pressure, shear force, and tissue temperature. Alternatively or additionally, the controller 58 receives a user input and regulates the fluid supply 14 as a function thereof. In some embodiments, the user input corresponds to a person's comfort level and is allowed to vary the surface performance index by ±5%. In some embodiments, the controller 58 regulates the fluid supply 14 as a function of environmental conditions, such as, ambient temperature and humidity.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described can be more desirable, the feature nonetheless is not intended to be necessary and embodiments lacking the same are contemplated as within the scope of the disclosure, including within the scope defined by the claims that follow.

In reading the claims it is intended that, when words such as "a," "an," "at least one," "at least a portion" are used, there is no intention to limit the claim to only one item unless specifically stated to the contrary in the claim. When the language "at least a portion" and/or "a portion" is used, the item includes a portion and/or the entire item unless specifically stated to the contrary.

While embodiments of the disclosure have been illustrated and described in detail in the drawings and foregoing description, the same are to be considered as illustrative and not restrictive in character, it being understood that only the selected embodiments have been shown and described and that all changes, modifications and equivalents that come within the spirit and scope of the disclosure as defined herein or by any of the following claims are desired to be protected.

The invention claimed is:

1. A person support surface comprising
at least one inflatable bladder,
a low air loss topper including a portion above the at least one inflatable bladder, and
a control system including a plurality of sensors that generate data signals indicative of a characteristic of the at least one inflatable bladder and a person's tissue supported above the low air loss topper, a processor operatively coupled to the plurality of sensors, the processor being configured to execute operating logic to determine a surface performance index as a function of the data signals, and a fluid supply coupled to the at least one inflatable bladder and to the low air loss topper, the processor controlling the operation of the fluid supply to deliver fluid flow through the low air loss topper as a function of the surface performance index to control at least one of convective evaporation and diffusive evaporation.

2. The person support surface of claim 1, wherein the control system is coupled to an electronic medical record (EMR) over a network and receives information from the EMR for use by the processor in controlling the operation of the fluid supply.

3. The person support surface of claim 2, wherein the information includes a Braden score.

4. The person support surface of claim 2, wherein the information includes at least one of pressure ulcer history and superficial lesion history.

5. The person support surface of claim 2, wherein the information includes at least one of height and weight.

6. The person support surface of claim 2, wherein the information includes an identification of the person's medication.

7. The person support surface of claim 1, wherein the surface performance index is a function of interface pressure, shear, and temperature.

8. The person support surface of claim 7, wherein the control system receives information regarding ambient conditions proximate the person support surface and the control system modifies the contributions of interface pressure, shear, and temperature to the surface performance index as a function of the information regarding the ambient conditions.

9. The person support surface of claim 1, wherein the processor uses a look up table to determine the surface performance index.

10. The person support surface of claim 1, wherein the control system is configured to adjust at least one of an operating parameter and characteristic of a therapy delivered by the fluid supply via the at least one inflatable bladder.

11. The person support surface of claim 10, wherein the therapy comprises at least one of low air loss therapy, percussion vibration therapy, and continuous lateral rotation therapy.

12. The person support surface of claim 1, wherein the control system alerts a caregiver if the fluid supply is unable to be operated to achieve the surface performance index.

13. The person support surface of claim 1, wherein the at least one inflatable air bladder comprises a plurality of inflatable air bladder that are grouped into zones, each zone being inflated by the fluid supply so as to achieve different surface performance indexes.

14. The person support surface of claim 1, wherein the control system operates to adjust a first pressure in the at least one air bladder to a second pressure, the second pressure being configured to lower the combined score $(P^2+S^2)^{1/2}$ in which P corresponds to a pressure measurement and S corresponds to a shear measurement.

15. The person support surface of claim 1, wherein at least one of a temperature, humidity, and flow rate of the fluid supplied by the fluid supply is adjustable.

16. The person support surface of claim 15, wherein at least two of a temperature, humidity, and flow rate of the fluid supplied by the fluid supply is adjustable.

17. The person support surface of claim 1, wherein the plurality of sensors comprise a pressure sensor, a shear sensor and a temperature sensor.

18. The person support surface of claim 17, wherein the plurality of sensors further comprise a humidity sensor.

19. The person support surface of claim 1, wherein the at least one bladder comprises a topper that extends over substantially an entire length and width of the person support surface.

20. A person support surface comprising
at least one inflatable bladder,
a cover including a portion above the at least one inflatable bladder, and
a control system including a plurality of sensors that generate data signals indicative of a characteristic of the at least one inflatable bladder and a person's tissue contacting the cover, a processor operatively coupled to the plurality of sensors, the processor being configured to execute operating logic to determine a surface performance index as a function of the data signals, and a fluid supply coupled to the at least one inflatable bladder, the processor controlling the operation of the fluid supply as a function of the surface performance index, wherein the processor uses the following equation to determine the surface performance index:

$$\text{Surface\_Performance\_Index} = \left[ \frac{\left(\frac{SPL_1}{SPL_{unloaded}}\right)}{\left(\frac{DMD_1}{DMD_{unloaded}}\right)} \right] =$$

$$\frac{\left[1.00 - \left[\frac{P_1^2 + S_1^2}{P_{occlusion}^2}\right]^{1/2}\right]}{(1+\%\_\text{reduction\_in\_tissue\_demand})\left(\left(\frac{tissue\_temp.\_°C.}{\frac{W}{m^2}}\right)*THW+37.78\right)}.$$

* * * * *